United States Patent [19]

Pelc

[11] Patent Number: 5,253,282
[45] Date of Patent: Oct. 12, 1993

[54] SYSTEM FOR SELECTIVE MATERIAL IMAGING

[75] Inventor: Norbert J. Pelc, Los Altos, Calif.

[73] Assignee: Lunar Corporation, Madison, Wis.

[21] Appl. No.: 874,146

[22] Filed: Apr. 27, 1992

[51] Int. Cl.⁵ ............................................... H05G 1/64
[52] U.S. Cl. ......................................... 378/99; 378/62; 378/96; 358/111
[58] Field of Search .................. 378/99, 96, 51, 54, 378/55, 62, 146; 358/111

[56] References Cited

U.S. PATENT DOCUMENTS

| | | | |
|---|---|---|---|
| 3,848,130 | 11/1974 | Macovski | 250/369 |
| 3,904,874 | 9/1975 | Amtmann et al. | 378/99 |
| 3,965,358 | 7/1976 | Macovski | 250/369 |
| 4,029,963 | 6/1977 | Alvarex et al. | 250/360 |
| 4,355,331 | 10/1982 | Georges et al. | 378/99 |
| 4,361,901 | 11/1982 | Daniels et al. | 378/106 |
| 4,542,459 | 9/1985 | Riederer | 378/99 |
| 4,947,414 | 8/1990 | Stein | 378/55 |
| 5,132,995 | 7/1992 | Stein | 378/55 |
| 5,148,455 | 9/1992 | Stein | 378/55 |

OTHER PUBLICATIONS

Simulation Studies of Dual-Energy X-Ray Absorptiometry, Sorenson et al., Med. Phys. 16(1), Jan./Feb. 1989.
Generalized Image Combinations in Dual KVP Digital Radiography, Lehmann, et al., Med. Phys. 8(5), Sep.-/Oct. 1981.

*Primary Examiner*—David P. Porta
*Attorney, Agent, or Firm*—Quarles & Brady

[57] ABSTRACT

A dual energy x-ray system for determining bone density and the like compensates for variable flux density associated with the different absorptions and the production of the high and low energies of x-rays by controlling both the voltage biasing the x-ray tube and the relative dwell times during which the x-ray tube is at those voltages, the dwell time being increased for the lower voltage to compensate for lower flux density. Compensation for variations in flux density improves the resultant signal-to-noise ratio of the measurements taken and thereby provides more accurate measurement of materials with minimized examination time.

5 Claims, 2 Drawing Sheets

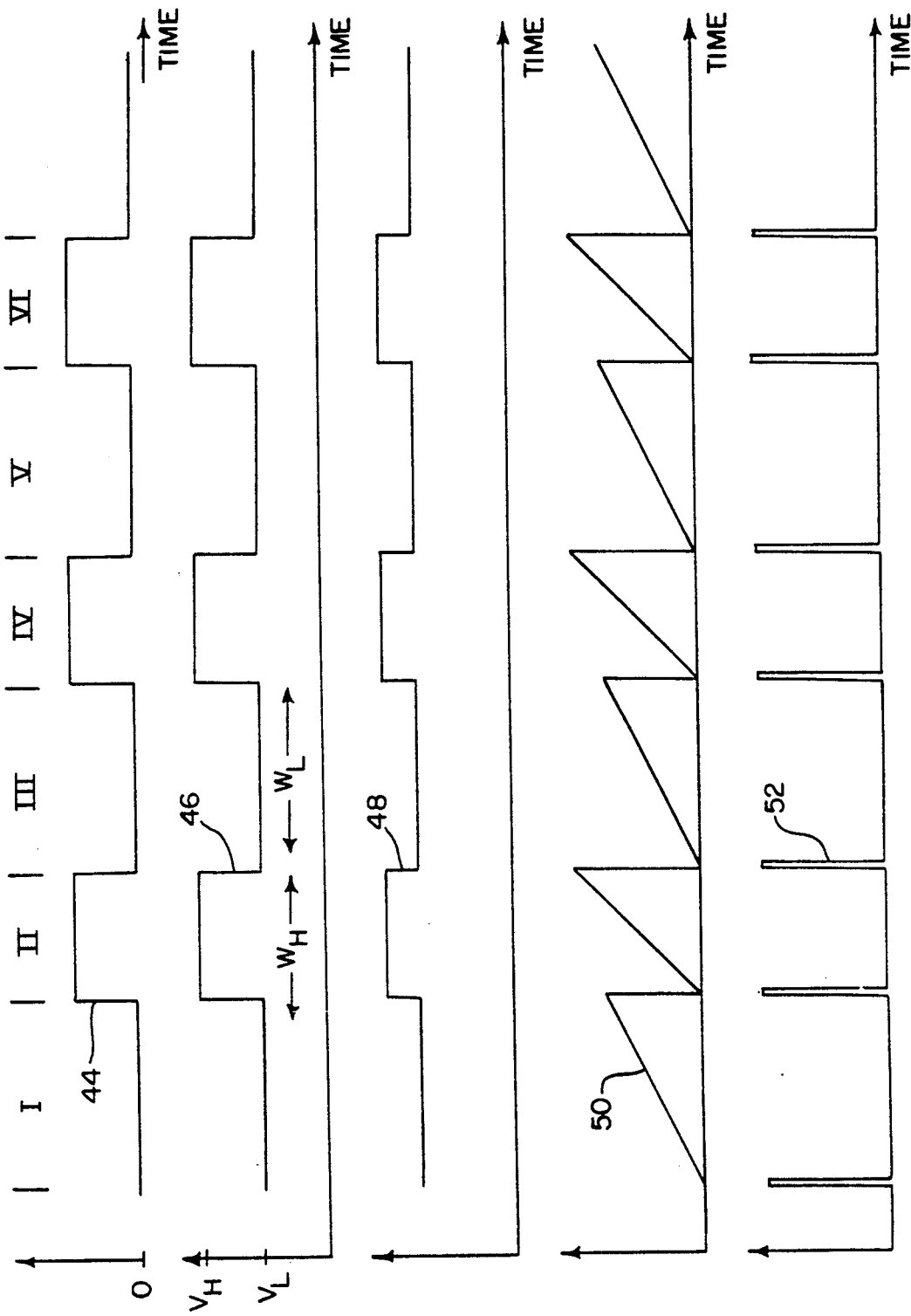

SYSTEM FOR SELECTIVE MATERIAL IMAGING

FIELD OF THE INVENTION

The present invention relates to the field of radiographic analysis of the human body and, in particular, to an x-ray system for selectively imaging materials within the human body.

BACKGROUND OF THE INVENTION

The x-ray absorption of a particular material depends on the energy of the x-ray photons directed through that material. Further, the functional relationship for x-ray absorption and x-ray energy differs between different materials.

The difference between absorption functions for different materials, that is, the difference in the relation between absorption and the x-ray energy, has been exploited to isolate the contribution of specific body materials to the absorption of x-rays along a given x-ray beam path. Quantitative measurement of the absorptions of single materials may be used to selectively image that material even if it overlaps with other materials along the direction of x-ray propagation.

This technique of selective imaging has been successfully applied, in one example, to measuring a patient's total bone mass and bone density in isolation from the patient's superimposed tissue mass. Bone density measurements are important in the treatment of bone diseases such as osteoporosis and in gauging the success of bone implants by evaluating the health of the bone in the neighborhood of the implant.

The difference in absorption functions for a given mass of two different body materials is primarily the result of two absorption mechanisms: photoelectric absorption and Compton scattering. Body materials may be distinguished by the degree to which each of these mechanisms contribute to their total x-ray absorption. It follows, also, that the absorption function for any body material may be accurately modeled by combining the functions for the photoelectric absorption and Compton scattering. This combination function is the sum of the photoelectric absorption and Compton scattering functions as weighted by coefficients unique to the particular material.

The ability to model the absorption of any material by a weighted combination of photoelectric absorption and Compton scattering is key to the selective imaging of materials. Selective imaging is accomplished by making two absorption measurements at two x-ray energies, and then, knowing in advance the coefficients associated with the body materials of interest, solving the resulting two independent equations to determine the total mass associated with each material. Although there are generally more than two body materials of interest, in many diagnostically important cases, the materials may be grouped in two categories, such as bone and tissue, which may be generally distinguished by these techniques.

A convenient way of producing the two energies of x-rays needed for selective imaging is by controlling the voltage of an x-ray tube. A typical x-ray tube consists of cathode which contains a heated filament and produces electrons which are directed toward a target anode. The cathode and anode are held in an evacuated envelope and a biasing voltage is placed across the cathode and anode to accelerate electrons toward the anode. A portion of the energy of the electrons incident on the anode is converted into x-ray radiation, the spectral content of which is dependent on the biasing voltage. Herein, the term "x-ray energy" will be used to mean the quantum energy of the photons that comprise the x-ray beam.

Accordingly, two different x-ray energies, and two different absorption measurements at those different energies, may be made simply by changing the voltage on the x-ray tube. The change in voltage across the x-ray tube also may be accompanied by the mechanical insertion of filters into the path of the x-rays. Filters preferentially absorb photons at certain x-ray energies and are used to increase the spectral separation of the two beams. Each voltage may have an associated filter or both may use the same filter.

In order to ensure that the two measurements of absorption, at the two energies of x-rays, are taken of the same portion of a patient, it is desirable that these measurements be taken in rapid succession. Otherwise, patient motion may corrupt the data. For scanning x-ray systems, where a narrow x-ray beam sweeps successively over different portions of the patient, the above condition requires that the beam of x-rays be repeatedly and rapidly switched between the two energy levels during its scan.

For each x-ray energy, a signal related to x-ray absorption is generated by a detector receiving the x-rays after they pass through the body. Common types of detectors are ionization chambers, scintillation detectors, and solid-state detectors which measure scintillations produced by the effect of x-rays passing through certain solid materials. Aside from the detection efficiency of the detector, the signal-to-noise ratio of the electrical signals produced by these detectors, and hence the quality of the selective imaging data, is predominantly a function of the flux density of the x-ray beams, that is, the number of x-ray photons per unit time per unit area at the object, which is transmitted through the object and detected.

Unfortunately, the flux density received by the detector can shift dramatically as the energy of the x-ray beam is changed. Generally, there is higher attenuation of x-rays by body materials at lower x-ray energies. Thus, the flux density of the x-rays received by the detector during the low energy portion of the measurement will be comparably reduced. This additional absorption is compounded by the fact that x-ray tubes are less efficient at lower energies and thus produce a lower flux density beam.

The signal-to-noise ratio of the resulting selective material image is a function of the signal-to-noise ratio of the measurements with each of the two beams. The measurement with the lesser signal-to-noise ratio of the high and low energy may disproportionately degrade the signal-to-noise ratio of the combined signals. Ideally the signal-to-noise ratios of the two measurements may be adjusted to optimize the quality of the final result for a given x-ray exposure to the patient. See, for example, Sorenson, Duke and Smith, Med. Phys. 16, p. 75–80, 1989.

Within the range of the sensitivity of the detector used to convert the x-ray beam to an electrical signal, the signal-to-noise ratio of the signal generated during the low energy portion of the scan may be selectively increased by increasing the flux density of the x-ray beam from the x-ray tube during that portion of the scan. This may be done, without appreciably changing the energy of the x-rays, by increasing the current flow in the x-ray tube while holding the anode to cathode voltage constant, i.e. increasing the cathode filament current and thus the cathode temperature.

For medical imaging, the benefit of increasing the flux density must be balanced by the need to reduce, to the extent possible, the total exposure of the patient to ionizing x-ray radiation. Therefore, it is desirable also, to reduce the flux density during the high energy portion of the scan. Again, this may be done by adjusting the cathode temperature, in this case by lowering the filament current.

Unfortunately, the cathode temperature may not be adjusted rapidly, and use of the cathode temperature to control the flux density of the x-ray beam prevents rapid change in beam energies as is needed to reduce patient motion problems. Slow switching speed also may significantly prolong the examination time in a scanning system and in all system results in needless exposure to the patient.

X-ray tube current can also be controlled by use of an x-ray tube with a grid and associated control circuitry. See, for example, U.S. Pat. No. 4,361,901. This significantly increases the complexity and cost of the x-ray source.

SUMMARY OF THE INVENTION

The present invention provides a means of rapidly switching between two x-ray beam energies, as required to reduce patient motion errors, while allowing control of the signal-to-noise ratio of the detector signals produced during the two energy measurements. In a system which periodically switches between high and low energy x-ray beams, flux density control is achieved by changing the relative dwell time during which the system is in each state.

Specifically, a clock produces a periodic signal having a first and second state, where the duration of the second state is longer than the duration of the first state. An x-ray tube controller supplies an x-ray tube with a high voltage when the clock signal is in the first state and a low voltage when the clock is in the second state to produce high and low energy x-ray beams respectively. A demultiplexer divides the electrical signal produced by a detector receiving the x-ray beams into two output signals: the first related to the value of the electrical signal during the first state, and the second related to the value of the electrical signal during the second state.

In one embodiment, the demultiplexer integrates the electrical signal so that the first and second output channel signals are proportional to the total x-ray radiation received by the detector during the first state and second state respectively.

It is one object of the invention to provide a mechanism for controlling the relative signal-to-noise ratios of the data sets acquired with rapidly switched x-ray systems. The present invention recognizes that the signal strength is proportional, not simply to flux density, but to the total number of x-ray photons measured. Thus, by changing the relative dwell time during which the tube is at the high and low energy levels, the signal-to-noise ratio of the signals detected for both states may be controlled.

It is another object of the invention to provide a means for minimizing the total examination time for measurements with rapidly switching x-ray systems. Alternative methods vary the beam current for each beam. This, in general, forces the beam current for at least one of the x-ray tube voltages to be less than the maximum allowed by the x-ray tube. The present invention allows the x-ray tube to be operated always at the maximum allowed beam current and does not limit the rate at which x-ray energy may be switched. This results in shorter measurement times and reduced effects from possible patient motion.

Other objects and advantages besides those discussed above shall be apparent to those experienced in the art from the description of a preferred embodiment of the invention which follows. In the description, reference is made to the accompanying drawings, which form a part hereof, and which illustrate one example of the invention. Such example, however, is not exhaustive of the various alternative forms of the invention, and therefore, reference is made to the claims which follow the description for determining the scope of the invention.

BRIEF DESCRIPTION OF THE DRAWINGS

FIG. 2 is graph showing the clock signals controlling the x-ray tube integrator and A/D of FIG. 1.

DETAILED DESCRIPTION OF THE PREFERRED EMBODIMENT

Figure 1:
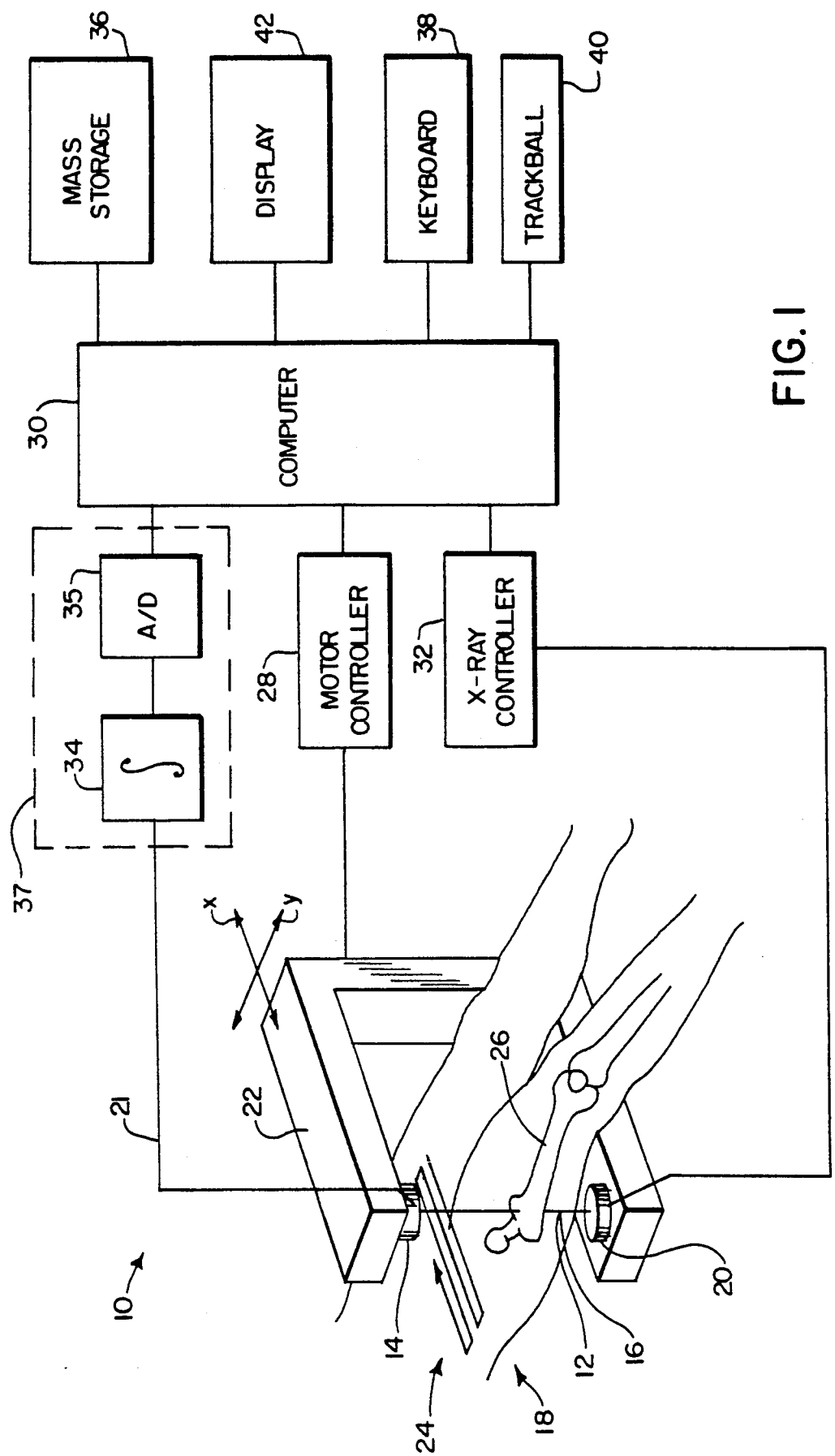
FIG. 1 is a schematic view of a scanning dual energy x-ray system suitable for use with the present invention showing the placement of the x-ray tube and the x-ray detector.

Referring to FIG. 1, a dual energy scanning x-ray machine 10 of a type which may be used with the present invention, projects a collimated x-ray beam 12 from an x-ray source 20 along a ray 16 through a patient 18 to an opposed detector 14. The x-ray source 20 and detector 14 are mounted on a carriage 22 to move in unison in a raster scan pattern 24 by means of stepper or servo motor (not shown). The raster scan pattern 24 sweeps the ray 16 over a rectangular area of the patient 18 by alternately directing it along one of two perpendicular axis x and y of a Cartesian coordinate system with the x-ray beam 12 parallel to a third orthogonal z axis.

The movement of the carriage 22 is controlled by a motor controller 28 receiving signals from a computer 30. The x-ray source 20 includes an x-ray tube filters (not shown) to create x-ray emissions. Computer 30 also controls the x-ray source 20, turning it on and off and switching voltages and/or filters by means of x-ray controller 32.

The signal 21 from the detector 14 is received and demultiplexed by integrator 34, digitized by A/D converter 35, and transmitted to computer 30 which stores the data in computer memory (not shown) or on mass storage device 36. An operator may provide inputs to the computer 30 by means of keyboard 38 and trackball 40, which allow positioning of a cursor on display screen 42, as is understood in the art. The display screen 42 also provides a means of displaying information obtained from the raster scan.

At a variety of discrete locations over the raster scan pattern 24, data are acquired from the detector 14 at each of two x-ray energies produced by the x-ray source 20, as switched by the x-ray controller 32. Thus, at each location, two data samples may be collected, having values corresponding to the absorption by the patient 18 of x-rays 12 at both of the x-ray energies. Each pair of samples may be identified to the x and y coordinate of the ray 16, along which the samples were acquired. Together, the sample pairs covering the entire raster scan pattern form elements of data matrices whose coordinates correspond to the spatial coordinates of the rays. On presently available scanning x-ray machines, as shown in FIG. 1, a spacing of 0.6 mm between samples may be obtained over a raster scan area of about 9 by 10 cm.

Referring to FIGS. 1 and 2, the x-ray controller 32 incorporates an internal clock (not shown) for generating a control signal 44, having a high state during periods II, IV and VI, and a low state during periods I, III, and V, for synchronizing the voltage supplied to the x-ray source 20 with the operation of data acquisition system (DAS) 37, comprised of integrator 34 and analog to digital (A/D) converter 35. Specifically, as shown in FIG. 2, when signal 44 is in the high state, the voltage 46 to the x-ray source 20 is increased to a high voltage, $V_H$, for a time period $W_H$ and when the signal 44 is in the low state, the voltage 46 to the x-ray source 20 is reduced to a low voltage $V_L$ for a time period $W_L$. The high and low voltages 46 on the x-ray source 20 refers to the voltage that biases the anode and cathode of the x-ray tube, as is generally understood in the art.

In the preferred embodiment, signal 44 also switches filters used to filter the x-ray beam. The changing voltage on the x-ray tube together with the filters, produces the two energy bands of x-ray emissions, as previously described. The narrow bands of x-ray emissions will be termed the high and low energy x-ray beams 12, respectively. The change in voltage 46 on the x-ray source 20 from a low to a high value will, due to space charge effects, cause an increase in beam current 48.

The radiation received by detector 14 from x-ray source 20 produces a signal current which is integrated in integrator 34 to produce a signal voltage 50. The integrator 34 is cleared at the beginning of time period I, and signal 50 increases during period I in proportion to the radiation intensity being detected by detector 14 in response to the low energy beam 12, dependent on x-ray tube voltage 46, current 48 and the patient 18 being measured.

A reset signal 52 derived from signal 44 comprises a short logic pulse having a rising edge during the transitions of signal 44 from either low-to-high level or from high-to-low level. On the rising edge of a pulse in signal 52, A/D converter 35 samples and digitizes signal 50, the output of integrator 34. Immediately after the sampling is complete, the pulse in signal 52 clears integrator 34.

During period II, the x-ray tube voltage 46 and current 48 are switched to their high states and integrator signal 50 increases at a rate dependent on the radiation intensity being detected by detector 14 in response to the high energy beam 12. The signal 50 is digitized at the end of period II. Thus, periods I and II together produce a pair of x-ray measurements. Similarly periods III and IV produce a pair of dual energy x-ray measurements, and so on. All of these digitized signals are stored by computer 30.

In FIG. 2, the values of integrated signal 50 are shown as being the same at the end of all the high voltage periods (II, IV, VI). Similarly, the values of signal 50 at the end of the low energy periods (I, III, V) are the same. This of course, is not generally the case. The values of integrated signal 50 depend on the details of the patient 12 through which beam 12 is transmitted, and on the raster scan movement of the x-ray beam 12.

Critical to the operation of the present invention is the choice of the time widths of the low and high energy time periods $W_L$ and $W_H$, respectively. The width of the low energy periods $W_L$ controls the integrated intensity of the low energy beam 12 during the low energy periods while $W_H$ controls the integrated intensity of the high energy beam 12 during high energy periods. By adjusting $W_L$ and $W_H$ the integrated intensities, and therefore the signal-to-noise ratios of the measurements, are controlled. This independent control of the signal-to-noise ratios of the low and high energy measurements allows optimization of the signal-to-noise ratio of the image of the selected material. The exact values of the $W_H$ and $W_L$ are determined by estimating the average attenuation provided by the patient 26 and adjusting $W_H$ and $W_L$ to obtain the optimal signal-to-noise ratios in the high and low energy measurements.

After one cycle of waveform 44, including a low state and a high state, absorption data has been collected for one point of the raster scan pattern 24 for both low and high energy x-ray beams 12. At this time, the stepper motors are actuated to move x-ray beam 12 to a new position on the body. It will be understood that at the completion of the raster scan pattern 24, arrays of digitized data elements will have been generated, each element associated with a particular point in the raster, and each array having values indicating the absorption of x-rays at high energy or the absorption of x-rays at low energy.

The data at two different x-ray energies associated with the high and low energy x-ray beams 12 can be used to separate the absorption effects of two different body materials at each point of the raster scan pattern 24 and thus to determine the mass of the different materials at each point in the array. Algorithms for converting measured x-ray data to selective material measurements are known in the art. See, for example, "Generalized Image Combinations in Dual kVp Digital Radiography" by Lehman, et al., Med. Phys. 8, (5), 1981, or the previously cited article by Sorenson et al. both hereby incorporated by reference.

It will occur to those who practice the art that many modifications may be made without departing from the spirit and scope of the invention. For example, techniques are known which use three or more x-ray measurements. The teaching of the present invention can be generalized to more than two measurements, the relative durations of the respective periods being controlled to adjust the relative integrated intensities detected with the various beams. Further, as described above, the widths of the time periods $W_L$ and $W_H$ are selected prior to the beginning of the scan, for example using knowledge of the object thickness and desired measurement precision. An alternative approach is to use feedback to automatically adjust $W_L$ and $W_H$. In this approach, the measured integrated intensities for the two beams are used to adjust the widths of the periods to maintain the desired measurement quality.

Finally, even with prospective selection of measurement periods, $W_H$ and $W_L$ control signal 44 need not be perfectly periodic. Different values of $W_L$ and $W_H$ can be used for different parts of the raster scan, for example, if it is known that part of the raster scan will examine the thicker portion of patient 12 than another portion. Also, the present invention can be used in systems which use a fan beam of radiation along with an array of detector elements and one dimensional scanning motion, or with area-beam systems which use no scanning motion at all.

In order to apprise the public of the various embodiments that may fall within the scope of the invention, the following claims are made.

I claim:

1. An apparatus for selective material imaging of an object including at least a first and second material comprising:

an x-ray tube for receiving a voltage and for producing x-ray radiation having spectral characteristics related to the voltage;

a timing control for defining a first state having a first duration and second state having a second duration different than the first duration;

an x-ray tube controller for supplying the x-ray tube with a high voltage during the first state and a low voltage during the second state;

a detector for receiving x-ray radiation from the x-ray tube as attenuated by the object and producing an electrical signal proportional to the intensity of the x-ray radiation;

a data acquisition system for receiving the electrical signal from the detector and for generating a first output channel signal related to the value of the electrical signal during the first state and for generating a second output channel signal related to the value of the electrical signal during the second state; and means for combining the first and second output channel signals to produce and image indicating substantially only the first material, wherein the first duration and second duration are selected to maximize the signal-to-noise ratio of the image.

2. An apparatus as recited in claim 1 wherein the data acquisition system integrates the electrical signal and wherein the first output channel signal is proportional to the total x-ray radiation received by the detector during the first state and the second output channel signal is proportional to the total x-ray radiation received by the detector during the second state.

3. The apparatus recited in claim 2 wherein the first and second durations are controlled by feedback of the first and second channel output signals.

4. An apparatus as recited in claim 1 wherein the data acquisition system integrates the electrical signal and wherein the first output channel signal is proportional to the total x-ray radiation received by the detector during the first state and the second output channel signal is proportional to the total x-ray radiation received by the detector during the second state.

5. A scanning x-ray system for selective material imaging of an object comprising:

an x-ray tube for receiving a voltage and for producing x-ray radiation having a beam area and with spectral characteristics related to the voltage;

a scanning means for scanning the beam area of the x-ray radiation at a plurality of points over the area of patient at a scan speed;

means for producing a control signal having a first state having a first duration and second state having a second consecutive duration different than the first duration at each point;

an x-ray tube controller for supplying the x-ray tube with a high voltage when the control signal is in the first state and a low voltage when the control signal is in the second state;

a detector for receiving x-ray radiation from the x-ray tube attenuated by the object and producing an electrical signal proportional to the intensity of the x-ray radiation; and a data acquisition system for receiving the electrical signal from the detector and for generating a first output channel signal related to the value of the electrical signal during the first state and for generating a second output channel signal related to the value of the electrical signal during the second state.

* * * * *